United States Patent

Prohaska

[11] Patent Number: 5,165,292
[45] Date of Patent: * Nov. 24, 1992

[54] CHANNEL DEVICE AND TUBE CONNECTION AND THEIR FABRICATION PROCEDURES

[75] Inventor: Otto J. Prohaska, Cleveland Heights, Ohio

[73] Assignee: OttoSensors Corporation, Mayfield, Ohio

[*] Notice: The portion of the term of this patent subsequent to Jul. 2, 2008 has been disclaimed.

[21] Appl. No.: 726,648

[22] Filed: Jul. 2, 1991

Related U.S. Application Data

[63] Continuation of Ser. No. 341,375, Apr. 21, 1989, abandoned, which is a continuation of Ser. No. 936,887, Dec. 2, 1986, abandoned.

[30] Foreign Application Priority Data

Dec. 9, 1985 [AT]  Austria .................. 3562/85

[51] Int. Cl.$^5$ .............................................. G01R 3/00
[52] U.S. Cl. ........................ 73/866; 55/386; 73/31.05; 73/54.04; 210/198.2; 210/198.3; 374/44
[58] Field of Search ............ 73/866, 864.83, 864.84, 73/54, 55, 56, 53, 23.2, 31.05, 31.06, 54.01, 54.04, 54.11, 53.01, 61.52, 61.58; 210/198.2, 798.3; 55/386; 374/44; 29/595, 621.1; 437/901, 8, 921

[56] References Cited

U.S. PATENT DOCUMENTS

| | | | |
|---|---|---|---|
| 3,503,116 | 3/1970 | Strack | 29/595 X |
| 3,538,744 | 11/1970 | Karasek . | |
| 3,696,479 | 10/1972 | Dias | 29/595 X |
| 4,064,753 | 12/1977 | Sun et al. | 324/688 X |
| 4,498,229 | 2/1985 | Wilner | 437/901 X |
| 4,542,650 | 9/1985 | Renken et al. | 73/204.26 X |
| 4,616,505 | 10/1986 | Jouwsma | 73/204.26 |
| 4,685,331 | 8/1987 | Renken et al. | 73/204.26 X |
| 4,729,189 | 3/1988 | Whitcomb | 47/79 X |
| 4,818,361 | 4/1989 | Burgess et al. | 204/415 X |
| 4,863,491 | 9/1989 | Brandt et al. | 210/198.2 X |
| 4,893,108 | 1/1990 | Kolesar, Jr. | 73/23 X |
| 4,902,138 | 2/1990 | Goeldner et al. | 374/44 |
| 5,027,499 | 7/1991 | Prohaska | 29/595 |
| 5,116,495 | 5/1992 | Prohaska | 210/198.2 |

FOREIGN PATENT DOCUMENTS

| | | | |
|---|---|---|---|
| 1113319 | 8/1961 | Fed. Rep. of Germany | 55/386 |
| 2049877 | 4/1972 | Fed. Rep. of Germany | 55/386 |
| 1364777 | 5/1964 | France | 55/386 |
| 18751 | 2/1981 | Japan | 73/31.05 |
| 103569 | 5/1987 | Japan | 55/386 |
| 2037066 | 7/1980 | United Kingdom | 55/382 |
| 2090768 | 7/1982 | United Kingdom | 210/198.2 |

Primary Examiner—Tom Noland
Attorney, Agent, or Firm—Calfe, Halter & Griswold

[57] ABSTRACT

A device for measuring at least one characteristic of a fluid is provided. The device comprises a measuring channel which is designed for conducting fluid flow therethrough and which is defined by a wall and a substrate. An inlet orifice and an outlet orifice are provided for conducting fluid into and out of the measuring channel and at least one sensor is located adjacent the measuring channel for measuring the characteristic of the fluid. The wall has outer portions, which are sealing adhered to the substrate, and upwardly bent portions, which partially define the measuring channel. The outer portions and the upwardly bent portions are of substantially the same thickness. The wall is preferably made of a synthetic resin, glass, ceramic, silicon nitride, silicon monoxide, silicon dioxide, or combination of these materials.

24 Claims, 4 Drawing Sheets

CHANNEL DEVICE AND TUBE CONNECTION AND THEIR FABRICATION PROCEDURES

This application is a continuation of U.S. application Ser. No. 07/341,375 filed on Apr. 21, 1989 (now abandoned) which was a continuation of U.S. application Ser. No. 06/936,887 filed on Dec. 2, 1986 (now abandoned).

FIELD OF THE INVENTION

The invention is concerned with a channel device for measuring and/or recording variables, such as thermal conductivity, viscosity, density, dielectric constants, refractive indices, etc., of materials such as fluids and gases (called samples). The material under investigation is guided through a measuring channel orifice for the sample. The invention also concerns the outlet fabrication procedure of the channel device, especially the recording unit for determining the thermal conductivity, viscosity, density, dielectric constant, etc. of samples wherein the material under investigation is passed through or brought into a measuring channel which is equipped with sensors and actuators.

BACKGROUND OF THE INVENTION

The aim of the invention is to create a measuring arrangement capable of on-line recordings which is extremely sensitive even for a very small sample volume and can be miniaturized for mass production, using photolithographic, thin-film and solid-state techniques.

SUMMARY OF THE INVENTION

The invention is characterized by a channel, formed by a substrate (or carrier) and a layer forming a wall, which is arranged a certain distance from the substrate. The layer is deposited by evaporation, spin-on, sputter, drop-on, reactive deposition, CVD, PECVD, etc., techniques. The layer is made of synthetic material, glass, ceramic, $Si_3N_4$, $SiO_2$, SiO, etc. and/or combinations of these materials. The invention is also characterized by the fact that the sensors and actuators are formed by layers on and/or in the substrate and/or in the wall forming layer. The sensors and actuator may be formed by techniques such as evaporation, spin-on, sputter, drop-on, reactive deposition, CVD (chemical vapor deposition), PECVD (plasma enhanced chemical vapor deposition), etc.

The process invention is characterized as follows: A dissolvable substance consisting of photoresist, synthetic material etc., is deposited on the substrate thereby forming the inside of the channel. The dissolvable substance is covered afterwards by the wall forming layer, which also covers at least parts of the substrate where the substrate is free of dissolvable substance. The layer adheres well on the substrate and forms, together with the substrate, the measuring channel. The dissolvable substance can be dissolved and removed through the inlet and outlet orifices using solvents and solutions which do not dissolve or attack the wall forming layer or the substrate.

Preferred or advantageous arrangements of the invention, as well as the detailed procedures, are to be found in the sub-claims, the descriptions and the schematic drawings.

Furthermore, it is the aim of the invention to establish connections to thin tubes in order to conduct fluids or gases in or out of the miniaturized measuring arrangements. At least one tube is connected to the substrate, such as by gluing. The invented tube connection is characterized by the fact that at least one layer is deposited in such a way that the endings of the tubes are kept open and the layer is tightly connected with the tube and the substrate. This establishes and defines a free space together with the substrate in such a way that this free space becomes a continuation of the inside of the tube. The at least one layer may be deposited by techniques such as evaporation, drop-on procedure, sputtering, spin-on, reactive deposition, CVD, PECVD. etc.

The fabrication procedure for such a connection according to the invention is characterized as follows. The tube may be mounted (i.e. glued) onto the substrate. A dissolvable substance, i.e. photoresist, synthetic resin, etc., is deposited onto a substrate as well as into a tube in such a way that this dissolvable substance forms a continuation of the tube. A layer is then deposited onto the dissolvable substance so that it covers this substance as well as at least a part of the tube and at least a part of the substrate. This layer forms a tight and sealing connection with the tube as well as with the substrate. The deposition of the layer may be performed by evaporation, drop-on, sputtering, spin-on, reactive deposition, CVD, PECVD, etc. The dissolvable substance can be dissolved and removed through the open end(s) of the tube and/or through the open end of the continuation which was formed by the dissolvable substance, using a solvent or procedure which will not affect the substrate or the layer or the tube.

Preferred designs of the tube connections and procedures for the fabrication of these connections can be found in the subclaims, the description and the drawings.

The evaluation and analysis of the measurements is performed by electronic devices which are connected to sensors and actuators which are arranged in and/or on the layer and/or in and/or on the substrate. The temperature rise of the heating layers, the creation of surface acoustic waves and all other actuations which are necessary for proper recordings, can be generated by appropriate electronic devices.

It is easy to see that recording arrangements, which are different from the ones described above, can be produced, using the invented fabrication techniques, i.e. miniaturized chromatographs, pH-meters, pressure sensors, etc.

The selection of the dissolvable substances and their solvents can, to a large extent, be left to specialists.

DETAILED DESCRIPTION

Figure 1:
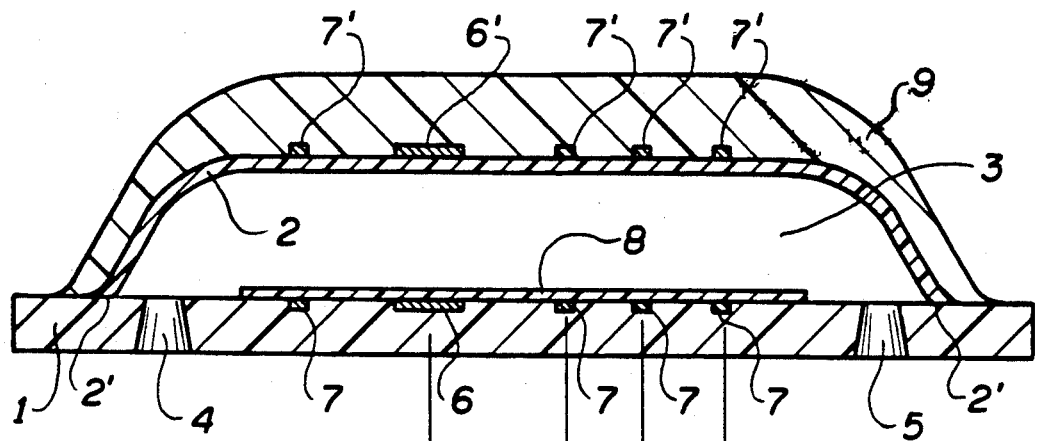
FIG. 1 shows a channel device which is especially designed for recording thermal conductivity and viscosity of a fluid or gas.

The schematic drawings explain the invention. FIG. 1 shows a channel device which is especially designed for recording thermal conductivity and viscosity of a fluid or a gas. A layer (2) is deposited on a substrate (I) in such a way that a measuring channel is formed which has at least one inlet orifice (4) and one outlet orifice (5).

The layer (2) is deposited onto the substrate (1) in the following manner. First, a dissolvable substance is deposited which has the shape of the measuring channel (3). On top of the dissolvable substance the layer (2) is deposited, covering the dissolvable substance and at least parts of the substrate (1) which may be called boundary parts (2'). The layer (2) adheres tightly to the boundary parts (2'). Then, the dissolvable substance is dissolved through inlet and/or outlet orifices (4,5). Thus, the measuring channel (3) is formed by the substrate (1) and the layer (2). The layer (2) includes opposite end portions (2') sealingly adhered to the substrate (1) and includes upwardly bent portions extending away from the substrate (1) to define the measuring channel (3) of a predetermined shape. The cross section of the measuring channel may be either rectangular or trapezoidal.

Actuators and/or sensors can be arranged on and/or in the substrate (1). Alternatively or additionally, actuators and/or sensors can be arranged on and/or in the layer (2). In this manner, the measuring channel (3) will be equipped with the desirable recording, sensing, and/or actuating units. The various sensor and/or actuator layers may be deposited before the deposition of the dissolvable substance. It is, however, possible to subsequently passivate the inside of the measuring channel (3) by inserting cover layers (8'') (See FIG. 1c). It is also possible to increase the measuring channel (3) by etching. It is further possible to modify the characteristics of the actuators and/or sensors by appropriate surface treatments.

Heating layers (6,6') are shown as an example in FIG. 1 in an indentation in the substrate (1) and on the layer (2). The layer (2) may be formed by evaporation, implantation, doping, etc. The electrical connections to these actuators are not shown. Temperature sensors (7,7') are arranged in the substrate (1) and on the layer (2). The temperature sensors (7,7') can consist of semiconductor layers, doped layers, metal layers, etc.

Figure 1B:
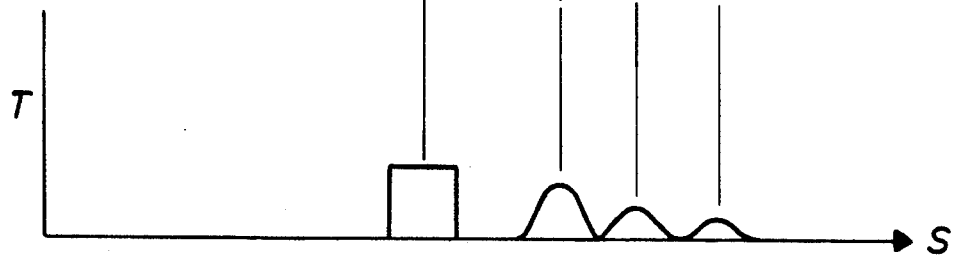
FIG. 1b shows a sample output of a viscosity measurement.
Figure 1A:
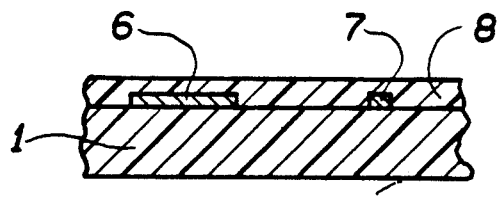
FIG. 1a shows a channel device with heating layers deposited on the substrate.
Figure 1C:
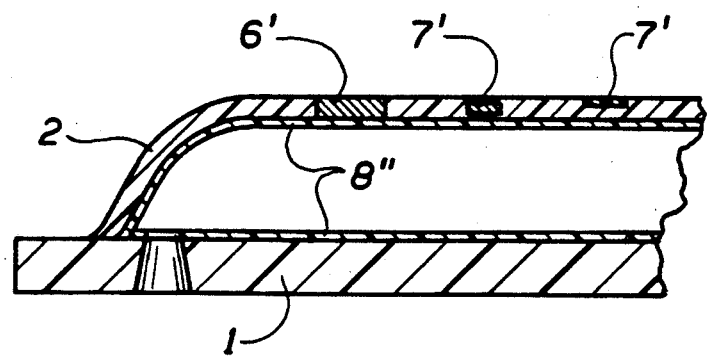
FIG. 1c shows the channel device of FIG. 1 including additional cover layers.

FIG. 1c shows the layers 6' and 7' as being contained in layer (2); and they can also be covered by a cover layer (8''). This arrangement is possible in particular if the layer (2) or the substrate (I) consists of silicon which can be formed into a sensor or actuator by doping or reactive deposition. In this case the layer (2) or the substrate (1) is part and/or basis for the sensor or actuator units.

The layers (6 and 7) can be deposited in indentations in the substrate (1) (See FIG. 1) or can be deposited on the substrate (1) (See FIG. 1a). The layers (6 and 7) can also be covered by a cover layer (8) in order to prevent modifications of the layers (6 and 7). Another layer (9) can be put on top of layer (2) and the layers (6' and 7'). The layer (9) can also be thicker to mechanically stabilize the channel device.

The deposition of the layers (2, 8, 9, 8', etc.) can be performed by drop on, or spread on, sputtering, evaporation, spin on, or other procedures.

The thickness of the layer (2) is advantageously between 1 $\mu$m and 50 $\mu$m, and the thickness of the layer (2) may be such that it forms a wall having a thickness which is equal to the height of the measuring channel. The height of the measuring channel (3) is from 0.01 $\mu$m to 50 $\mu$m, the width of the measuring channel (3) can be between 1 $\mu$m and 500 $\mu$m and the length of the measuring channel (3) might be up to several mm. These values can be changed, however, depending on the various applications. In most cases it might be advantageous to have the height of measuring channel (3) much smaller than the width in order to provide an optimum contact between the sample and the sensors and actuators. The thickness of the sensor and actuator layers is usually in the range of 0.2 $\mu$m and 40 $\mu$m.

Figure 11:
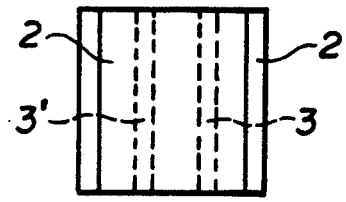
FIG. 11 shows a device including a reference measuring channel.

The viscosity measurement (FIG. 1b) is performed by applying a heat pulse through the heating layer (6,6') onto the sample gas or liquid which flows through the measuring channel, and measuring the resulting temperature change of the sample with the temperature sensors 7 and/or 7'. The time between the heat pulse application and the temperature change, measured with the sensors 7 or 7', determines the velocity of the sample in the solution which, in turn, is in inverse proportion to the viscosity. The pressure difference between the inlet (4) and outlet (5) of the measuring channel (3) has to be known or controlled and can be measured with pressure sensors (7''). Pressure sensors can be avoided in case of using a reference measuring channel (3) and the same pressure difference in both channels. (See FIG. 11)

Thermal conductivity can be measured by applying a certain amount of heat onto the material being tested and detecting such application at the temperature sensors (7). See FIG. 1c.

All the explanations for FIG. 1 are in principle valid for the following figures and the described characteristics can be combined with the any of devices shown in these figures.

Figure 2:
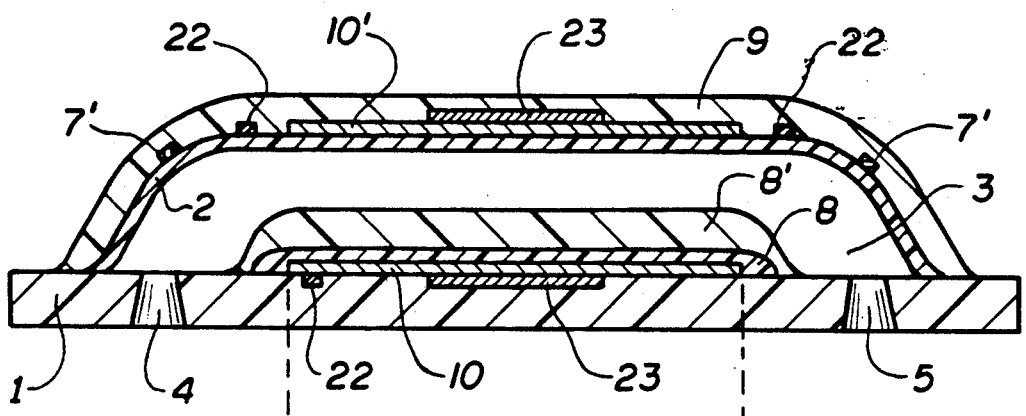
FIG. 2 shows a channel device for recording viscosity and/or dielectric constants.
Figure 2A:
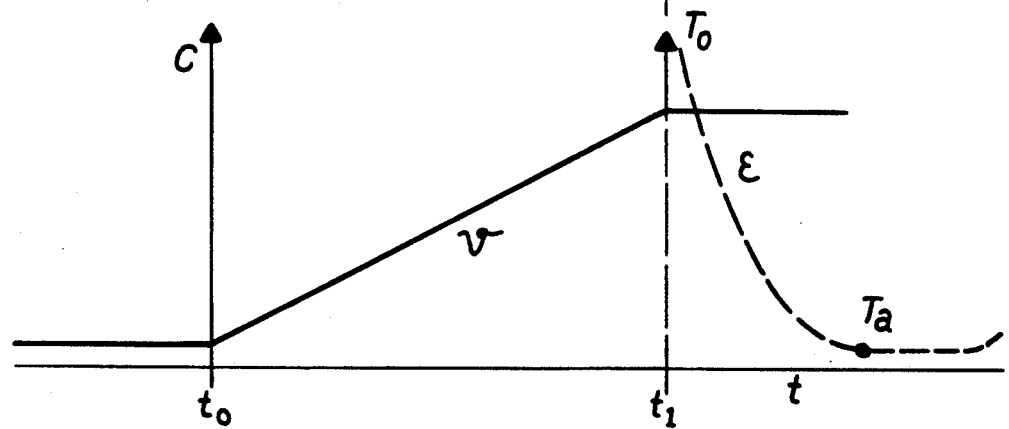
FIG. 2a shows the change in the capacitance of the layers as the samples moves into and through the measuring channel of the channel device of FIG. 2.

FIG. 2 shows a channel device for recording viscosity and/or dielectric constants. This channel device is in principle designed similar to the one described in FIG. 1 and includes conducting layers (10,10') deposited on a substrate (1) and a layer (2), thereby forming a capacitor. As soon as the sample moves into and through the measuring channel (3), which was previously filled with air or was evacuated, the capacitance of the layers (10,10') will be changed, as shown in FIG. 2a. The slope of the capacitance change is proportional to the velocity of the sample in the measuring channel (3) and permits the calculation of the viscosity.

It is advantageous, and increases the accuracy of the device, if the height of the measuring channel (3) has the same value as the thickness of the cover layer (8') in FIG. 2.

The dielectric constant can be determined from the capacitance of the device as soon as the measuring channel (3) is completely filled with the sample.

Figure 2B:
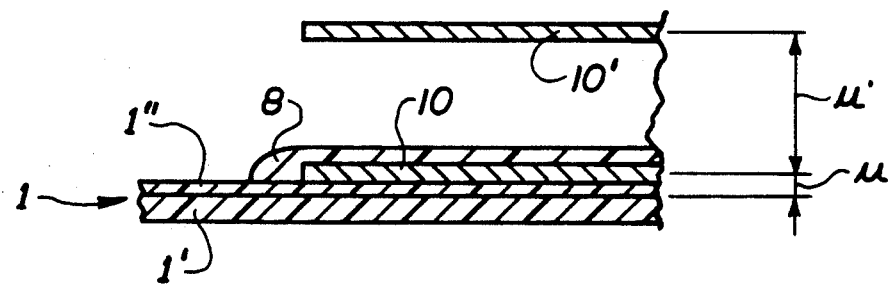
FIG. 2b shows a possible design of the channel device.

FIG. 2b shows a possible design of the channel device wherein the substrate (1) consists of a basic material (i.e. silicon or p-doped Si) (1') topped by an n-doped layer (1"), forming a barrier layer. Viscosity and dielectric constant measurements can be performed as described above.

Figure 3:
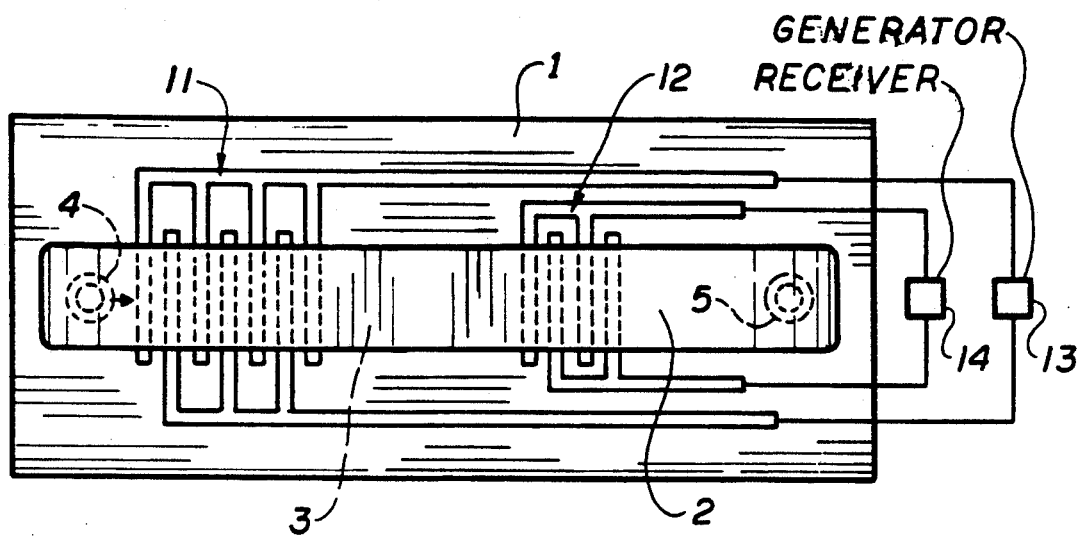
FIGS. 3 and 3a show a channel device for performing density measurements.
Figure 3A:
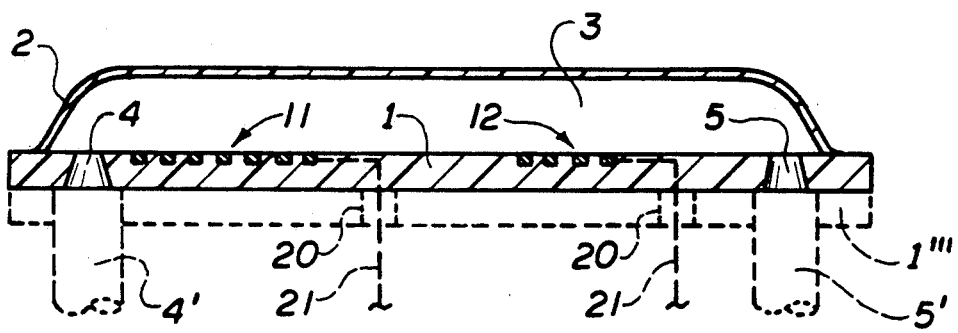

Density measurements of the sample can be performed by the device shown in FIG. 3 and FIG. 3a. Transmitter layers 11 and receiver layers (12) are arranged on indentations or on the surface of a piezoelectric substrate. The transmitter layers 11 are connected to one or more high frequency generators 13 which supply 20 to 50 kHz in the low voltage range and which generate surface acoustic waves in the substrate 1. The resonance signal is detected by the receiver layer (12) which is connected to a receiver 14. The signal can be changed or damped in dependance of the density of the sample in the measuring channel.

Figure 4:
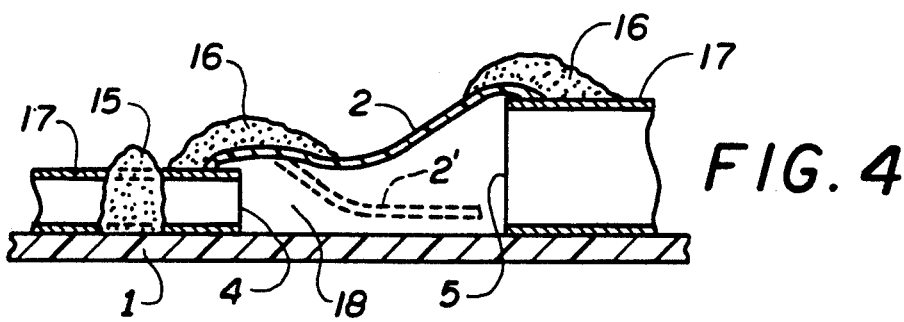
FIG. 4 shows two tubes connected to the substrate by an adhesive layer.

FIG. 4 shows two tubes (17) connected to the substrate (1), i.e. by an adhesive layer (15). The two tubes (17) are connected to a layer (2) which forms a channel (18) with the substrate (1), adhering tightly to the tubes (17) and the substrate (1) as well. The transition between the layer (2) and the tubes (17), kinks, exposed bends, etc. can be strengthened mechanically by supporting layers (16) consisting of the same material or a material different from that of layer (2). The fabrication of such a connection is performed by depositing a dissolvable substance onto the ends of the tubes (17) and onto the substrate (1) with the desired shape of the channel (18). The shape of the dissolvable substance can be obtained, for instance, by photolithographic processes. The layer (2) will be deposited onto the dissolvable substance in such a way that the layer (2) forms a tight connection with the tubes (17) and the substrate (1). The dissolvable substance will be dissolved through the tubes (17). This technique allows the design of connections between and to tubes of various, especially very small, dimensions.

Figure 5:
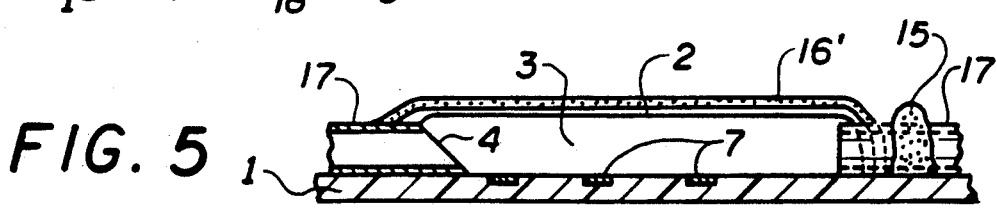
FIG. 5 shows a design appropriate to forming inlet and outlet orifices of the measuring channels.

FIG. 5 shows a design, appropriate to forming inlet and outlet orifices (4,5) of measuring channels(3). The tubes (17) replace the orifices (4,5) in the substrate (1). The design of the measuring arrangement with sensors and actuators can be as described in FIGS. 1 to 3. The layer (2) can be covered by a protective layer (16') which can be deposited in the same way as layer (2) consisting of the same, or a different material (i.e. glue), as layer (2). The endings of the tubes (17) can be tilted.

Figure 6:
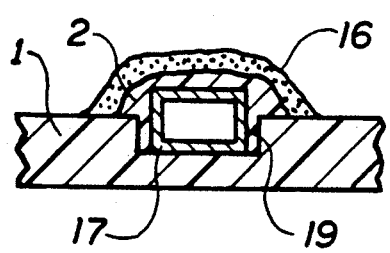
FIG. 6 shows that the tubes may be covered by a layer and thereby tightly connected to the substrate.

FIG. 6 shows that the tubes (17), especially their endings, can be covered by the layer (2) and thereby tightly connected to the substrate (1). The layer (16) can be of additional support and increase the adhesion of the tubes (17) to the substrate (1). FIG. 6 also shows the tubes (17) can be placed in indentations (19) in the substrate (1). The cross section of the tubes (17) can be of any shape, i.e. round, rectangular, etc. As shown in FIG. 6, the cross section of the indentation 19 corresponds substantially to the cross section of the tube 17.

Figure 7:
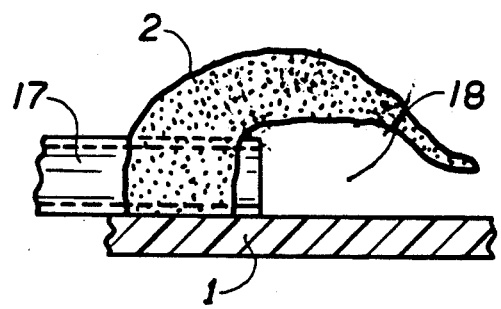
FIG. 7 shows a special continuation being shaped at this part like a nozzle.

The same techniques which permit the production of tube connections also permit the fabrication of special tube continuations (see FIG. 7). A tube (17) which can be connected by an adhesive layer to a substrate (1) will be covered at its one ending by a dissolvable substance which also covers the substrate (1), being especially shaped at this part, i.e. like a nozzle. The layer (2) will be deposited onto at least part of the tube (17), at least parts of the dissolvable substance and at least parts of the substrate (1). The dissolvable substance will be dissolved, leaving a nozzle-like continuation of the tube (17), formed by the layers (2) and the substrate (1), and which can be used, for instance, for injection of substances into the body tissue, etc. A similar nozzle-like extension of the tube (17) is also shown in FIG. 4, created by the layer (2'), which can be mechanically protected and/or strengthened by an additional layer (16).

Figure 8:
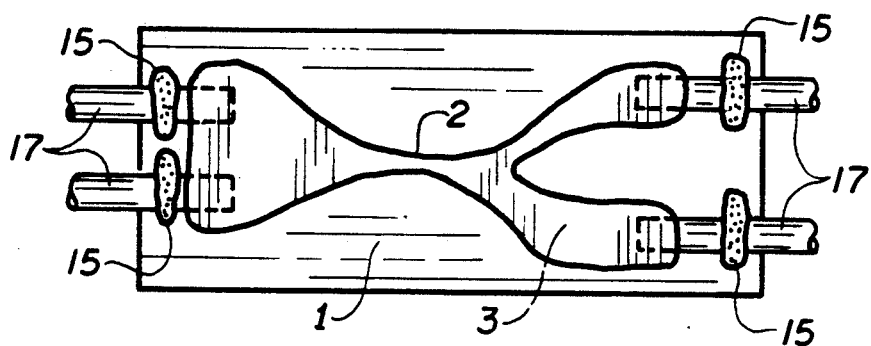
FIG. 8 shows several tubes which are not necessarily arranged in parallel, and which are connected by a channel which is formed by a layer and a substrate.

FIG. 8 shows several tubes (17) which are not necessarily arranged in parallel and which are connected by a channel (3). The channel (3) is formed by the layer (2) and the substrate (1). The endings of the tubes (17) on the left-hand side of FIG. 8 are combined by the measuring channel (3) of decreasing cross sections. The measuring channel (3) finally splits up into several channels each of which can have a different cross section and each of which can be connected to a tube (17). The described invention allows the fabrication of almost any kind of bifurcation, cross section and channel shape in order to establish connections of, and among, numerous tubes thus creating the possibility of forming valve-like control elements, flow regulators, etc.

It is also possible to etch the measuring channel (3) as shown in FIG. 8 into the substrate (1) in order to achieve a smooth transition between the tubes (17) and the measuring channel (3). Preferable diameters of the tubes (17) for the described fabrication procedures are in the range between 5 $\mu$m and 500 $\mu$m. It is also possible to connect two tubes (17) with each other which are placed next to each other or located in such a way that their ends are almost touching each other.

The invented channel devices and the tube connections can be used for investigations of body and tissue liquids, and for delivery of substances (i.e. to various nerves, organs, etc.). The invented channel devices may also be used for industrial applications, such as ink jet recorders, fuel injection systems, or other devices wherein pipe systems consisting of fine tubes have to be connected to each other or external macroscopic supply systems. A big advantage of the invention is also that the described channel devices yield precise results also in case of extremely small sample volumes, representing unique measuring units regarding response time, accuracy, resolution and reproductability.

The materials forming the layer (2) or (16) can consist of organic substances, such as synthetic resin, polymers, epoxy resin, etc. or any other organic substances such as $Si_3N_4$, $SiO_2$, $SiO$, $SiC$, etc. or substances with similar mechanical and or electrical qualities.

The connections to the sensors and actuators can be established by thin film interconnect paths, deposited in similar ways as described above.

It is, of course, possible that one measuring channel (3) contains several sensors, actuators and/or combinations thereof which can be arranged on and/or in the substrate (1). Alternatively or additionally, these several sensors, actuators and/or combinations thereof maybe arranged on and/or in the layer (2).

Light sources and light detectors can be used for refraction index measurements. Light can be, for instance, transferred through a light permeable layer (2) and light detectors may measure reflected and/or transmitted light intensities. These measurements may be used, for instance, to calculate the refraction index of the sample. The light can also be transmitted through the tubes (17) or the tubes (17) can be replaced by optical fibers.

All these values, of course, can be used in order to determine and analyze the composition of the sample.

Figure 9:
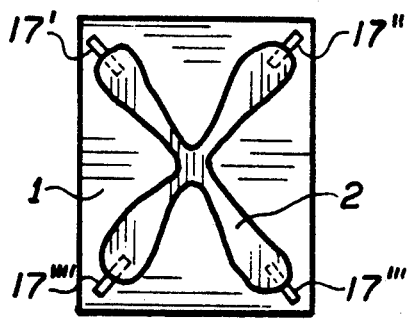
FIG. 9 shows a channel device for flow regulation.
Figure 9A:
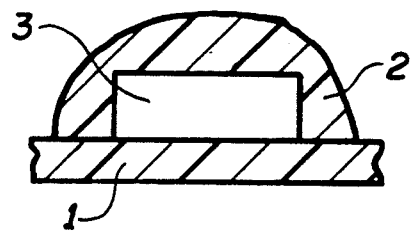
FIG. 9a shows the cross section or a measuring channel having a rectangular cross section.
Figure 10:
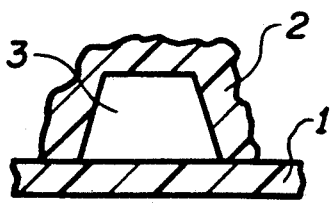
FIG. 10 shows the cross section of a measuring channel having a trapezoidal cross section.

FIG. 9 shows a device for flow regulations. The flow of a sample, i.e. from tube (17') to tube (17") in the channel formed by layer (2), can be changed or totally directed into the tube (17'$^v$). Miniaturized valve and flow control units can be fabricated.

FIG. 3a shows, in dashed lines, the connections of the substrate (1) to a supporting substrate (1'''). The supporting substrate could be an IC socket consisting of a gold plated surface which can be in a well known way sealed to a Si substrate (1). Tubes can be soldered to the substrate (1''') forming inlet (4') and outlet (5') orifices for the measuring channel (3). The sensors can be connected via wires (21) through ceramic feed throughs (20).

A temperature sensor (22) and a heating layer (23) is shown in FIG. 2b allowing evaporation heat measurements. The channel is filled with a sample and the temperature of the sample is measured. The evaporating sample attracts evaporation heat from the environment, which can be measured by the sensor (22). The temperature slope is shown in FIG. 2a by the dashed line. The evaporation heat can be calculated from the time course of the temperature between $T_0$ (temperature in the beginning of the measurement when the measuring channel is filled with the sample) and $T_1$ (end temperature when the measuring channel is empty). Capacitance measurements can be performed at the same time, determining the amount of the substance in the channel.

It is obvious that sensors and actuators, as shown in FIG. 2, can be arranged next and/or above each other.

One may now appreciate that the invention discloses the construction of a channel device for the recording of thermal conductivity, viscosity, density, dielectric constant, etc. of liquids and/or gases (sample), where the sample is directed through a measuring channel, with at least one inlet and one outlet orifice, containing at least one sensor unit and is characterized in that a measuring channel is established by the substrate and a layer, forming a wall, which is arranged in a certain, predetermined distance and fabricated i.e. by evaporation, spin on, sputtering, drop on, etc. procedures, where the layers can consist of synthetic resin, glass, ceramic, etc. and in that measuring units are deposited in layers in and/or on the substrate and/or in and/or on the wall forming layer.

One may now appreciate that the invention also discloses the fabrication procedure for the channel device, characterized in that a dissolvable substance (i.e. photoresist, synthetic resin, etc.) is deposited on a substrate, forming the inside of the measuring channel, on top of which a wall forming layer is deposited (i.e. by spin on, drop on, evaporation, etc. techniques) where the layer not only covers at least part of the dissolvable substance but also at least a part of the substrate. The wall forming layer adheres well on the substrate 15 and forms the measuring channel together with the substrate. The dissolvable substance can be dissolved and removed through the inlet and/or outlet orifices of the measuring channel.

One may now appreciate that the invention discloses furthermore a tube connection, characterized in that at least one tube, which can be connected with the substrate i.e. by gravity forces, glue, etc. is covered by a layer, formed by drop on, evaporation, sputtering, spin on, etc. procedures and which forms a tight seal with the tube and the substrate. The tube ending is kept open by the layer that, together with the substrate, forms a cavity which represents a continuation of the tube.

One may now appreciate that the invention also discloses the fabrication procedure of the tube connector, characterized in that on a substrate and at least one tube, which can be connected to the substrate, i.e. by a glue, a dissolvable substance, i.e. photoresist, synthetic resin, etc. is deposited forming a continuation of the tube. A layer is deposited on top of at least part of the dissolvable substance and on at least part of the tube and at least part of the substrate by i.e. drop on, sputtering, spin on, etc. techniques which is tightly adhering on the tube and substrate; afterwards, the dissolvable substance is dissolved and removed through the tube or the orifice of the tube continuation, which is formed by the layer and the substrate.

I claim:

1. A device for measuring at least one characteristic of a fluid, said device comprising:
    means defining a measuring channel of predetermined shape for conducting fluid flow therethrough;
    an inlet orifice and an outlet orifice for conducting the fluid into and out of said measuring channel;
    at least one sensor located adjacent said measuring channel for measuring the one characteristic of the fluid;
    said means defining said measuring channel including a substrate and a wall having opposite end portions sealingly adhered to said substrate, said wall including upwardly bent portions extending away from said substrate to define said measuring channel of a predetermined shape;
    said device further comprising one tube attached to said substrate and defining said inlet orifice, and a second tube attached to said substrate defining the outlet orifice; said wall tightly adhering to at least part of both of said tubes defining said inlet and outlet orifices upon being attached to said substrate.

2. A device as set forth in claim 1 wherein said wall is made of a material selected from the group consisting of a synthetic resin, glass, ceramic, silicon nitride, silicon monoxide, silicon dioxide, or combination of these materials.

3. A device as set forth in claim 1 further comprising an actuator for acting on the fluid during measuring the characteristic thereof.

4. A device as set forth in claim 3 wherein said actuator includes at least one heating element for heating the fluid and said one sensor is a temperature sensor.

5. A device as set forth in claim 4 wherein said temperature sensor is located between said one heating element and said outlet orifice.

6. A device as set forth in claim 4 wherein said temperature sensor is located between said heating element and said inlet orifice.

7. A device as set forth in claim 1 wherein said one tube defining said inlet orifice forms a nozzle.

8. A device as set forth in claim 1 further comprising an additional layer at least partially covering said wall.

9. A device as set forth in claim 8 wherein said substrate has an indentation for receiving at least one of said tubes therein.

10. A device as set forth in claim 9 wherein the cross-section of said indentation corresponds substantially to the cross-section of said one tube.

11. A device as set forth in claim 1 further comprising more than two tubes communicating with said measuring channel, said measuring channel having a plurality of channel portions associated with respective tubes and having different cross-sections.

12. A device as set forth in claim 1 wherein the height of said measuring channel is from 0.01 um to 50 um and the width of said measuring channel is equal to or greater than its height.

13. A device as set forth in claim 1 further comprising a cover layer for protecting said one sensor.

14. A device as set forth in claim 1 wherein said one sensor is positioned on the outside of said wall and is protected with a cover layer.

15. A device as set forth in claim 1 further comprising a reference channel for comparison measurement of a reference sample.

16. A device as set forth in claim 1 wherein the thickness of said wall is equal to the height of said measuring channel.

17. A device as set forth in claim 1 wherein the cross-section of said measuring channel of a shape selected from a group consisting of a rectangle and a trapezoid.

18. A device for measuring at least one characteristic of a fluid, said device comprising:
means defining a measuring channel of predetermined shape for conducting fluid flow therethrough;
an inlet orifice and an outlet orifice for conducting the fluid into and out of said measuring channel;
at least one sensor located adjacent said measuring channel for measuring the one characteristic of the fluid;
said means defining said measuring channel including a substrate and a wall having opposite end portions sealingly adhered to said substrate, said wall also including upwardly bent portion extending away from said substrate to define said measuring channel of a predetermined shape;
wherein said inlet and outlet orifices are formed by holes extending through said substrate.

19. A device as set forth in claim 18 wherein said wall is made of a material selected from the group consisting of a synthetic resin, glass, ceramic, silicon nitride, silicon monoxide, silicon dioxide, or combination of these materials.

20. A device as set forth in claim 18 further comprising an actuator for acting on the fluid during measuring the characteristic thereof.

21. A device as set forth in claim 18 wherein said actuator includes at least one heating element for heating the fluid and said one sensor is a temperature sensor.

22. A device as set forth in claim 21 wherein said temperature sensor is located between said one heating element and said outlet orifice.

23. A device as set forth in claim 18 wherein the height of the measuring channel is from 0.01 $\mu$m to 50 $\mu$m and the width of said measuring channel is equal to or greater than its height.

24. A device for measuring at least one characteristic of a fluid, said device comprising:
means defining a measuring channel of a predetermined shape for conducting fluid flow therethrough;
an inlet orifice and an outlet orifice for conducting fluid into and out of said measuring channel;
at least one sensor located adjacent said measuring channel for measuring the one characteristic of the fluid;
said means defining said measuring channel including a substrate and a wall having opposite end portions sealingly adhered to said substrate, said wall also including upwardly bent portions extending away form said substrate to define said measuring channel of a predetermined shape, said measuring channel being formed by depositing said wall by one of evaporation, spin on, drop on, sputtering, reaction deposition, chemical vapor deposition, and plasma enhanced chemical vapor deposition onto a portion of said substrate and onto at least a portion of a dissolvable body of material previously deposited on said substrate and having the predetermined shape of said measuring channel, the dissolvable body of material being subsequently dissolved and removed to form said measuring channel between said wall and said substrate, said wall remaining adhered to said substrate during and after dissolving of the dissolvable body of material.

* * * * *